US011174131B1

(12) United States Patent
Gonzalez

(10) Patent No.: US 11,174,131 B1
(45) Date of Patent: Nov. 16, 2021

(54) SANITIZING SYSTEM FOR HANDRAILS

(71) Applicant: Beatris Gonzalez, Miami, FL (US)

(72) Inventor: Beatris Gonzalez, Miami, FL (US)

( * ) Notice: Subject to any disclaimer, the term of this patent is extended or adjusted under 35 U.S.C. 154(b) by 0 days.

(21) Appl. No.: 17/061,497

(22) Filed: Oct. 1, 2020

(51) Int. Cl.
B66B 31/02 (2006.01)
A61L 2/18 (2006.01)
A61L 2/26 (2006.01)

(52) U.S. Cl.
CPC ............ *B66B 31/02* (2013.01); *A61L 2/18* (2013.01); *A61L 2/26* (2013.01); *A61L 2202/14* (2013.01); *A61L 2202/15* (2013.01)

(58) Field of Classification Search
CPC ... B66B 31/02; A61L 2/18; A61L 2/26; A61L 2202/14; A61L 2202/15
See application file for complete search history.

(56) References Cited

U.S. PATENT DOCUMENTS

| 7,854,313 | B1 | 12/2010 | Gotsche | |
|---|---|---|---|---|
| 9,039,842 | B2 | 5/2015 | Holloway | |
| 2005/0217971 | A1* | 10/2005 | Kim | B66B 31/02 198/338 |
| 2010/0060550 | A1* | 3/2010 | McGinn | G06F 3/1454 345/2.1 |
| 2017/0217735 | A1* | 8/2017 | Ibrahim | B66B 31/02 |
| 2020/0384141 | A1* | 12/2020 | Kim | A61L 2/10 |

FOREIGN PATENT DOCUMENTS

| DE | 2505874 A1 * | 8/1976 |
|---|---|---|
| JP | 2012082054 | * 10/2010 |

OTHER PUBLICATIONS

Derwent Abstract 2012-E73221 for JP 2012082054 (Year: 2010).*
English abstract for DE 2505874 A (Year: 1976).*

* cited by examiner

*Primary Examiner* — Sean E Conley
(74) *Attorney, Agent, or Firm* — Sanchelima & Associates, P.A.; Christian Sanchelima; Jesus Sanchelima

(57) ABSTRACT

A sanitizing system including a housing assembly and a sanitizing assembly is disclosed. The housing assembly includes a housing having lights thereon. Attached to a top of the housing is a display to present news, alerts or advertisements to users approaching an escalator or walkway with moving handrails. The housing including a curvature at a rear side that cooperates with the handrails, allowing the housing to be secured to the handrails. Within the housing is a container of the sanitizing assembly having a sanitizing solution within. The sanitizing solution is dispensed onto a sanitizing roller attached to the housing. The sanitizing roller is in abutting contact with the handrails to constantly deliver the sanitizing solution to the handrails and eliminate cross contamination bacteria from the handrails. The sanitizing roller engages a top end and lateral sides of the handrails ensuring that the handrails are always cleaned between users.

20 Claims, 5 Drawing Sheets

SANITIZING SYSTEM FOR HANDRAILS

BACKGROUND OF THE INVENTION

1. Field of the Invention

The present invention relates to a sanitizing system and, more particularly, to a sanitizing system for handrails that automatically and constantly maintains the handrails cleansed and sanitized even during constant usage.

2. Description of the Related Art

Several designs for sanitizing systems for handrails have been designed in the past. None of them, however, include a sanitizing system including a dispensing member attached to the handrails that is constantly sanitizing the handrails, additionally and simultaneously users may inform of various news in real time with a display that provides notices and alerts.

Applicant believes that a related reference corresponds to U.S. Pat. No. 9,039,842 for a moving handrail sanitizing device. Applicant believes that another related reference refers to U.S. Pat. No. 7,854,313 for an escalator handrail sanitizer. None of these references, however, teach of a system for sanitizing handrails that constantly sanitizes handrails and can also be used to keep users informed of real time news with alerts and notices.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide a sanitizing system that constantly sanitizes handrails.

It is another object of this invention to provide a sanitizing system that can be used by users to selectively sanitize themselves.

It is still another object of the present invention to provide a sanitizing system that can be retrofitted onto existing handrails.

It is also another object of the present invention to provide a sanitizing system that provides notices and alerts to users.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
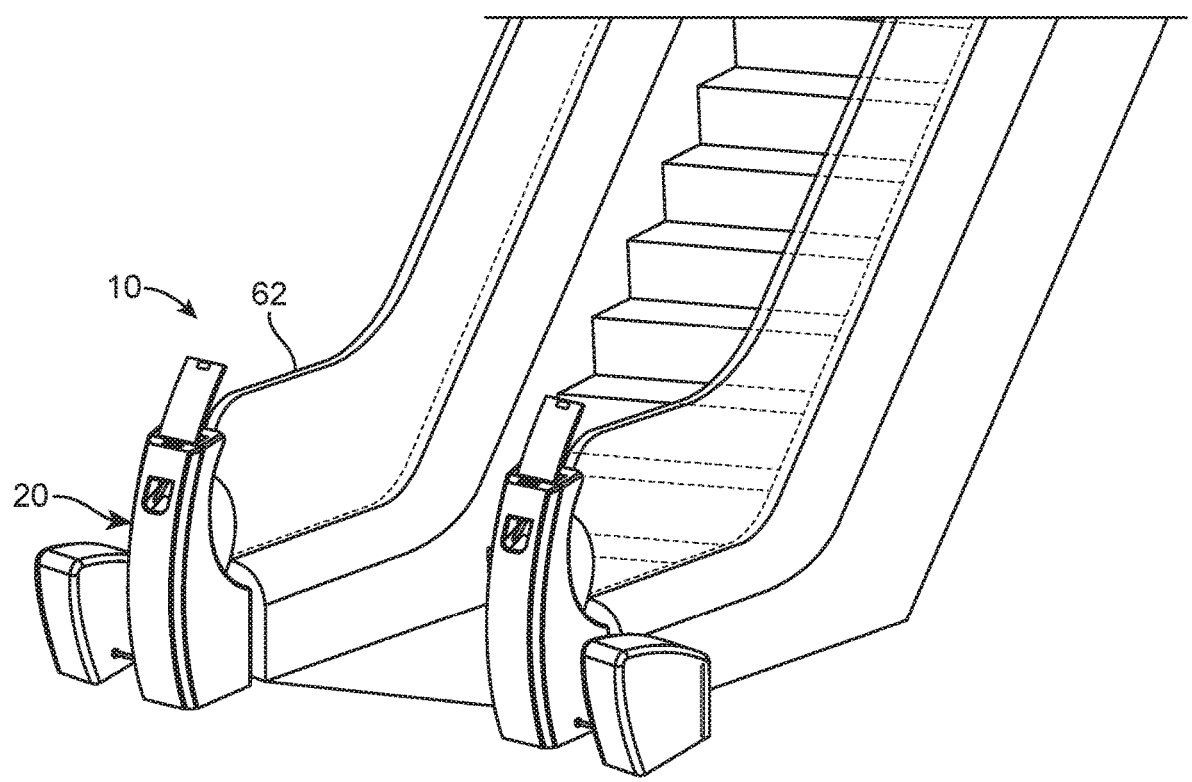
FIG. 1 represents an operational view of the sanitizing system 10 secured to a handrail 62 of an escalator.

Referring now to the drawings, where the present invention is generally referred to with numeral 10, it can be observed that a sanitizing system 10 basically includes a housing assembly 20 and a sanitizing assembly 40.

Figure 2:
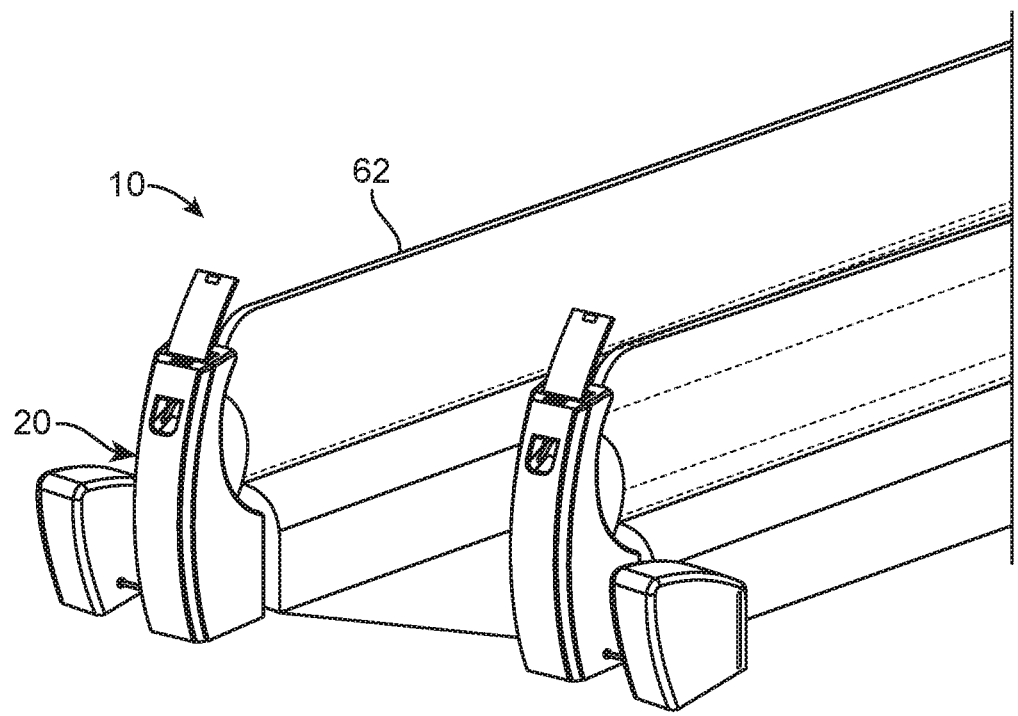
FIG. 2 shows another operational view of the sanitizing system 10 secured to a handrail 62 of a moving walkway.
Figure 3:
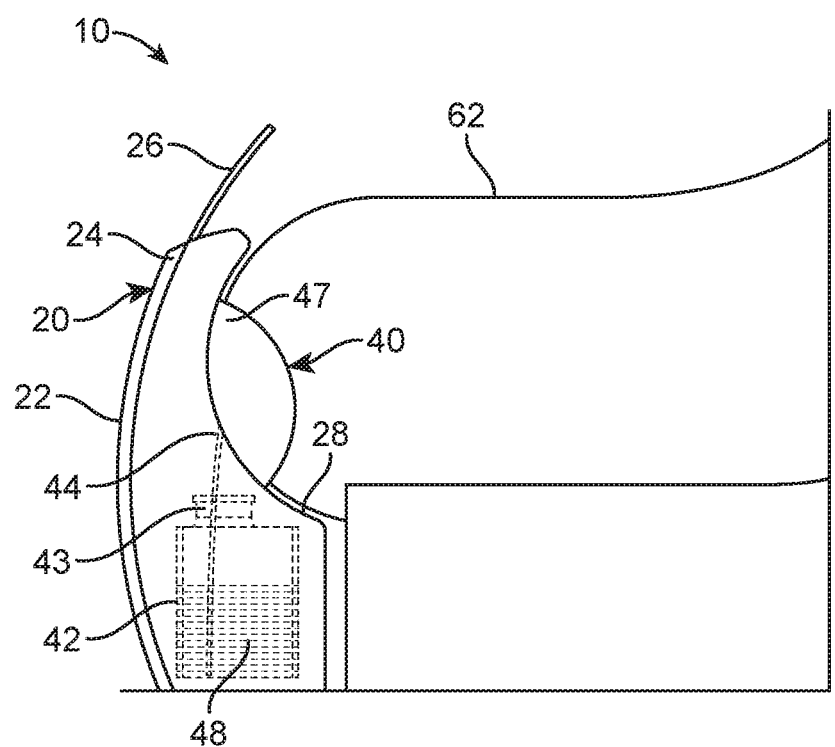
FIG. 3 illustrates a sideview of the sanitizing system 10 secured to a handrail 62 of an escalator.
Figure 4:
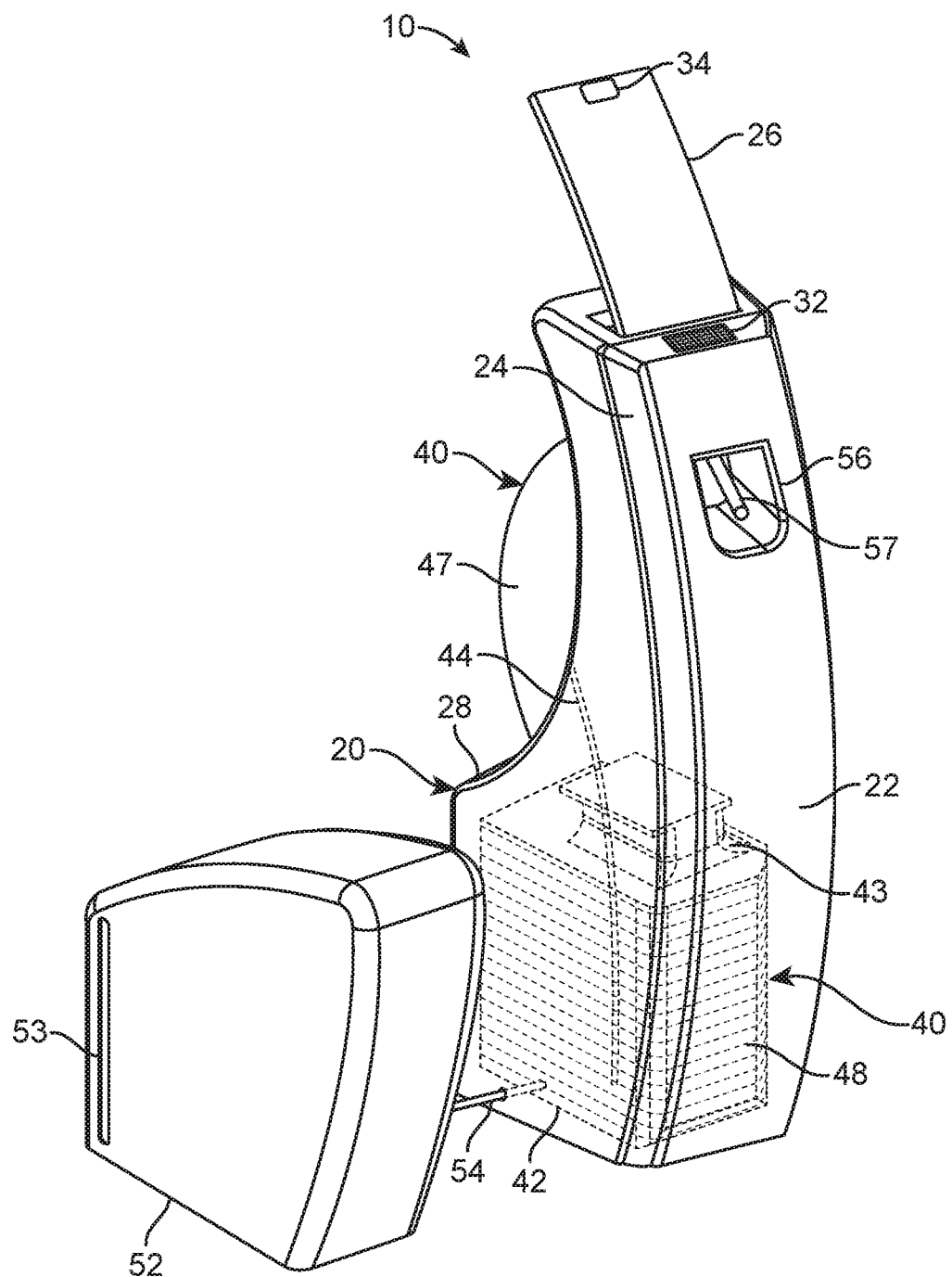
FIG. 4 is a representation of an isometric view of the sanitizing system 10.
Figure 5:
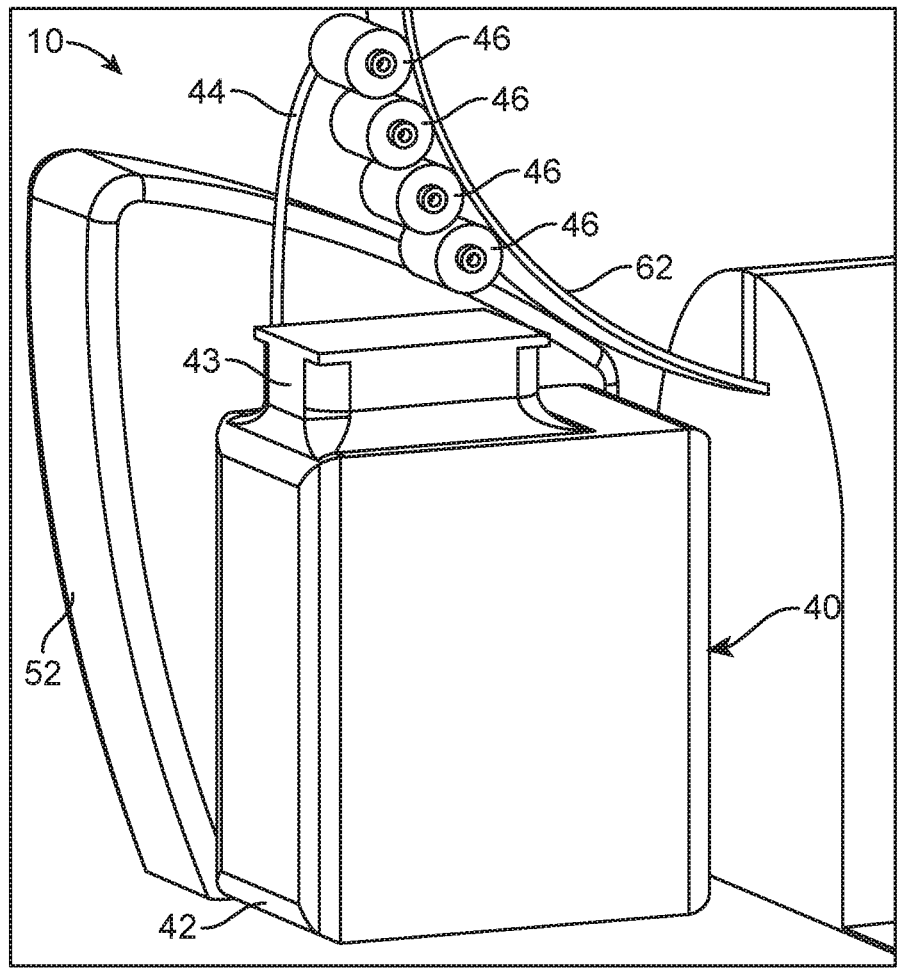
FIG. 5 represents an isometric view of housing 22 removed to expose sanitizing assembly 40, more specifically, showing how sanitizing rollers 46 engage handrail 62 and at least one of sanitizing rollers 46 being in fluid communication with container 42 with the help of hose 44 for dispersing of sanitizing solution 48. It is to be understood that the sanitizing rollers 46 are supported by housing 22 which was removed for illustrative purposes.
Figure 6:
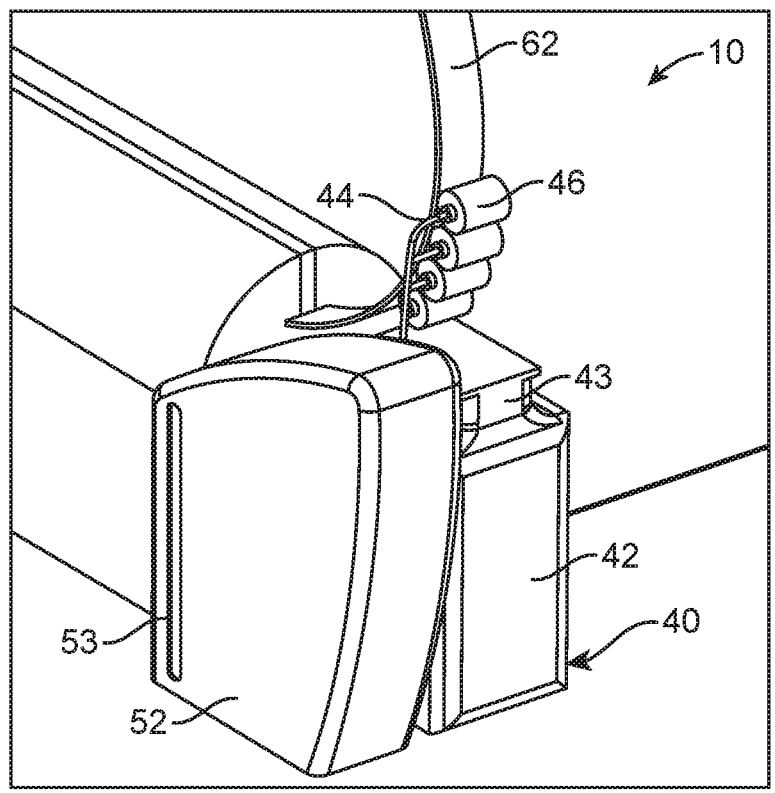
FIG. 6 represents an isometric view of housing 22 removed to expose sanitizing assembly 40, more specifically, showing how sanitizing rollers 46 engage handrail 62 and all of sanitizing rollers 46 being in fluid communication with container 42 with the help of hose 44 for dispersing of sanitizing solution 48. It is to be understood that the sanitizing rollers 46 are supported by housing 22 which was removed for illustrative purposes.
Figure 7:
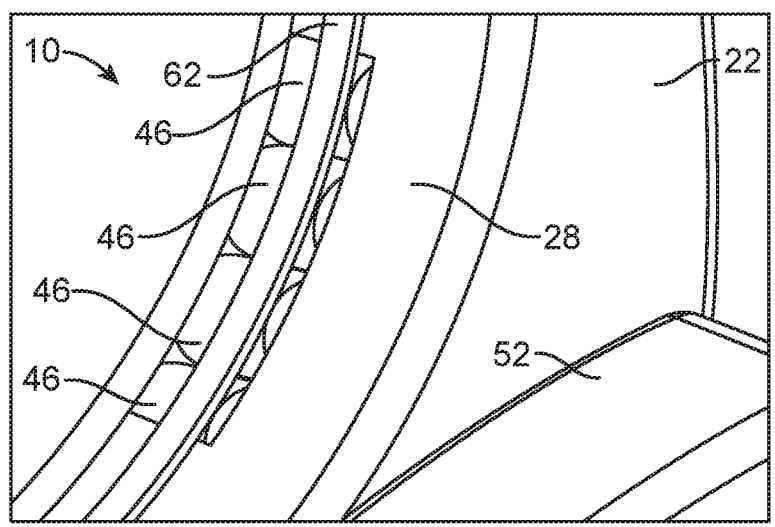
FIG. 7 represents a rear view of housing 22 showing sanitizing rollers 46 partially exposed from housing 22 and in abutting contact with handrail 62 for sanitation thereof.

Diseases, germs or bacteria are constantly located on surfaces, which can lead to illnesses being transferred from one person to another. The transfer of illnesses occurs more frequently when there are surfaces which are commonly shared between people. A handrail 62 of an escalator or a walkway, as best illustrated in FIGS. 1 and 2, respectively, is constantly in usage and as such constantly being touched. The touching of handrail 62 causes for handrail 62 to be festered with diseases. Sanitizing system 10 may be secured to handrail 62 to constantly sanitize handrail 62 to eliminate the transfer of diseases, viruses or bacteria. It is to be understand that additional of handrail 62 may require additional of sanitizing system 10 attached thereto. The increase in the sanitation of handrail 62 helps to increase the health of users.

Housing assembly 20, as best illustrated in FIGS. 1-4, may be secured to handrail 62. It is to be understood that within housing assembly 20 may be secured sanitizing assembly 40. Housing assembly 20 may include a housing 22. Housing 22 may be attached adjacently and in abutting contact with handrail 62. It is to be understood that housing 22 may have a predetermined elongated shape. Housing 22 may extend vertically, in one embodiment. Housing 22 may be made of materials such as plastic, aluminum, metal, rubber or other suitable materials. It is to be understood that housing 22 may have a height greater than a length of width thereof.

Located about lateral front sides of housing 22 may be lights 24. In one embodiment, lights 24 may be LED lights or light strips. Lights 24 may change colors as desired users, the color of lights 24 may be customizable. It may be suitable for lights 24 to be steady or flash in a predetermined pattern. Lights 24 may help users to more easily locate handrails 62. Additionally, lights 24 may also bring attention to the fact that handrails 62 are constantly being sanitized by sanitizing system 10. It is to be understood that lights 24 may be connected to a power source for energy to function.

Secured to a top of housing 22 may be a display 26. Display 26 may be used to provide real time news or information to users. Display 26 may provide alerts or notices to users about information regarding their surroundings, in one embodiment. In an alternate embodiment, display 26 may be used for advertising. It may be suitable for display 26 to be connected to the internet to be able to present real time information. Display 26 may be located at a top distal end of housing 22. Display 26 may be received in a slot located at the top distal end of housing 22. The slot may extend the width of housing 22. In one embodiment, display 26 may retract in and out of the slot. It is to be understood that display 26 may extend outwardly and away from housing 22. In the preferred embodiment, display 26 may be rectangular and extend upwardly. It is to be understood that display 26 may extend slanted and rearwardly towards the rear side of housing 22. Display 26 may be a screen, in one embodiment. Display 26 may alternatively be an advertising board, in an alternate embodiment, used to display various stationary advertisements to users. Secured to housing 22 and in cooperation with display 26 may be at least one speaker 32 and at least one camera 34. Speaker 32 may emit sounds that correspond with what is being depicted on display 26. Speaker 32 may also emit music, in one embodiment. It is to be understood that speaker 32 may be adjacent to display 26. It may be suitable for speaker 32 to be below of display 26. It may be suitable for speaker 32 to extend a partial length of display 26. Camera 34 may help to capture a video or pictures of users as they approach the escalator or handrail 62. The contents captured by camera 34 may be displayed on display 26. Alternatively, the contents captured by camera 34 may be sent to a remote location for safety monitoring and/or storage. Preferably, camera 34 may be secured to display 26 along a top end thereof. Camera 34 may extend partially along the length of display 26. In an alternate embodiment, camera 34 may be adjacent to display 26. It is to be understood that within housing 22 may be a power source and other electrical components to allow proper function of display 26, speaker 32 and camera 34. In an alternate embodiment, housing 22 may include a microphone to allow for communication between users and a person at a remote location.

Importantly, at a rear side of housing 22 may be a curvature 28. Curvature 28 may cooperate with a curve of handrail 62. Curvature 28 permits for housing 22 to be secured to a front of handrail 62 in abutting contact therewith. Curvature 28 may extend and curve away from lights 24. Curvature 28 permits handrail 62 to continue rolling without any obstructions. It is to be understood that curvature 28 may be where sanitizing assembly 40 is secured to. Curvature 28 may extend a partial height of housing 22.

Sanitizing assembly 40, as best illustrated in FIGS. 1-4, may help to constantly sanitize handrail 62. Sanitizing assembly 40 may include a container 42. Container 42 may preferably be enclosed within housing 22. Container 42 may be of a predetermined shape that cooperates with fitting entirely within housing 22. In the preferred embodiment, container 42 may be of a similar shape as housing 22. In an alternate embodiment, container 42 may be secured to an exterior of housing 22. It is to be understood that within container 42 may be a sanitizing solution 48 that may be used to cleanse and sanitize handrail 62. Sanitizing solution 48 may help to eliminate viruses, diseases or bacteria located on the surface of handrail 62. Thereby preventing for diseases, viruses or bacteria to be transmitted between people interacting with handrail 62. Secured atop of container 42 may be a compartment 43. Compartment 43 may be used to store necessary components for the function of the presentation invention such as a pump for dispensing of sanitizing solution 48, a timer to determine every how often sanitizing solution 48 is to be dispensed, and electrical components such as a processor and the like. Container 42 may be in constant abutting contact with compartment 43.

A hose 44 may be attached to container 42. One distal end of hose 44 may be in communication with container 42. At an opposite distal end hose 44 may be attached to at least one of sanitizing rollers 46 to deliver sanitizing solution 48 thereto. It is to be understood that sanitizing rollers 46 may be secured at a rear of housing 22 at curvature 28. Sanitizing rollers 46 may be centrally located along curvature 28. Sanitizing rollers 46 may be partially exposed at a rear of housing 22 to allow sanitizing rollers 46 to be in constant abutting contact with handrail 62. Sanitizing solution 48 may be dispensed on at least one of sanitizing rollers 46, preferably the topmost of sanitizing rollers 46, with hose 44. Sanitizing solution 48 may then drip downwardly onto the remaining of sanitizing rollers 46. In an alternate embodiment, each of sanitizing rollers 46 may be attached to hose 44 to be soaked by sanitizing solution 48 individually. Sanitizing solution 48 may entirely soak sanitizing rollers 46. Sanitizing rollers 46 may then be used to cleanse and deliver sanitizing solution 48 to handrail 62. Sanitizing rollers 46 may all engage an outer surface of handrail 62 simultaneously. In an alternate embodiment, sanitizing rollers 46 may engage the lateral sides of handrail 62 as well. As handrail 62 rotates, sanitizing rollers 46 simultaneously rotate as well. It may be suitable for sanitizing rollers 46 to use energy from the rotation of handrail 62 to also rotate. Upon sanitizing rollers 46 rotating, sanitizing solution 48 is released onto handrail 62. It is to be understood that sanitizing rollers 46 may alternatively be a brush. In an alternate embodiment, sanitizing solution 48 may be dispensed from container 42 directly onto handrail 62 as a mist from hose 44. The mist from hose 44 may be constant as handrail 62 is constantly being rotated away from housing 22. Thereby ensuring that handrail 62 is constantly sanitized to increase the health and safety of users. It is to be understand that a pump may be secured to container 42 which may cause sanitizing solution 48 to flow through hose 44 for dispensing thereof. In yet another embodiment, sanitizing rollers 46 may be replaced or supplemented by an ultraviolet (UV) light, an ultraviolet-a (UVA) light or an ultraviolet-c (UVC) light. It is to be understood that the UV light, UVA light or UVC light may be housed within housing 22. Radiation emitted from the UV, UVA or UVC light may be used to sanitize handrails 62. The radiation may help to eliminate the germs, viruses or diseases located on handrail 62. Thereby resulting in handrail 62 being sanitized by contactless means.

On the periphery sides of curvature 28 may be guards 47. Guards 47 may help to keep users from making direct contact with sanitizing rollers 46. Guards 47 may be semicircular in shape in one embodiment. Guards 47 may be parallel to each other. Guards 47 may extend outwardly and away from curvature 28. Guards 47 may partially cover the sides of handrail 62. Sanitizing rollers 46 may be located between guards 47.

Optionally, to aid in reducing the frequency in which container 42 is refilled with sanitizing solution 48, an external container 52 containing additional of sanitizing solution 48 may be secured to container 42. External container 52 may have a rearwardly sloping shape. Wherein external container 52 includes a front portion that is taller than a rear portion thereof. External container 52 may slope downwardly from the front portion to the rear portion along a top portion thereof. External container 52 may be substantially rectangular shaped. External container 52 may be adjacent to housing 22. An external hose 54 may extend between and may be used to interconnect container 42 and external container 52 together, in one implementation. It may be suitable for container 42 to be adjacent to and in abutting contact with external container 52, in one implementation, with a very short of external hose 54. Container 42 may be in fluid connection with external container 52 to allow sanitizing solution 48 from external container 52 to flow into container 42 for dispensing thereof. External container 52 helps to increase the capacity of the present invention for sanitizing solution 48. Thereby helping to reduce the chance that handrail 62 goes without being sanitized. External container 52 may be filled with sanitizing solution 48 through an opening sealed by a container lid, in one embodiment. External container 52 may be of predetermined dimensions and be made of a similar material as container 42. External container 52 may include a container viewing window 53 that allows viewing of the contents of external container 52. Container viewing window 53 may help to determine when there is a need to refill external container 52 with additional of sanitizing solution 48. Container viewing window 53 may extend a height of the rear portion of external container 52, in one embodiment.

Sanitizing system 10 may further allow users to directly sanitize themselves. A sanitizer dispenser 56 may be secured to housing 22. Sanitizer dispenser 56 may be recessed within housing 22 in a cavity of housing. Sanitizer dispenser 56 may be entirely below display 26 in one embodiment. Preferably, sanitizer dispenser 56 may be secured to a front of housing 22. It is to be understood that sanitizer dispenser 56 may be in fluid communication with container 42 for dispensing of the sanitizing solution 48 within directly onto users when actuated. Thereby allowing users to additional sanitize their hands before making contact with handrail 62. Sanitizer dispenser 56 may dispense sanitizing solution 48 with a nozzle 57. It may be suitable for sanitizer dispenser 56 may be actuated by motion or touch from users. In an alternate embodiment, sanitizer dispenser 56 may house an independent bag or pouch with additional of sanitizing soliton 48 to be dispensed within. Sanitizer dispenser 56 may include a door leading to an interior of sanitizer dispenser 56, when opened, for refilling thereof. Additionally, sanitizer dispenser 56 may include a viewing window allowing for viewing of how much of sanitizing solution 48 remains within sanitizer dispenser 56. The viewing window of sanitizer dispenser 56 facilitates determining when sanitizer dispenser 58 needs refilling with additional of sanitizing solution 48 if not interconnected to container 42. The viewing window may be secured to the door. The viewing window may allow viewing of the interior of sanitizer dispenser 56 when the door is closed.

Sanitizing system 10 helps to eliminate bacteria, germs or viruses on handrail 62 by constantly sanitizing handrail 62 with sanitizing solution 48. Thereby helping to increase the health of users by reducing the chance of cross contamination from handrail 62. Sanitizing system 10 helps to provide a peace of mind to users by reducing anxiety over fears of becoming ill from touching a common touched surface. Additionally, sanitizing system 10 helps to keep users informed about the latest real time news.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A sanitizing system, comprising:
   a. a handrail;
   b. a housing assembly including a housing, said housing including a curvature on a rear side that cooperates with a shape of said handrail, said housing being secured to said handrail; and
   c. a sanitizing assembly including sanitizing rollers secured entirely within the periphery of the rear side of said housing along said curvature, said sanitizing rollers being entirely on the same plane and centrally located along said curvature adjacent to each other, said sanitizing rollers soaked in a sanitizing solution, wherein a cut portion is formed onto the rear side of housing exposing each of the sanitizing rollers thereof, wherein a hose is operatively coupled to a lateral side of each of the sanitizing rollers thereof, said sanitizing rollers being in abutting contact with said handrail to dispense said sanitizing solution onto an outer surface of said handrail as the handrail rotates for sanitation of said handrail.

2. The system of claim 1, wherein said sanitizing assembly includes a container secured within said housing containing said sanitizing solution within.

3. The system of claim 2, wherein said container is entirely below said curvature, said sanitizing rollers being entirely above of said container.

4. The system of claim 2, wherein the hose is attached in fluid communication with said container and said sanitizing rollers, said hose delivering said sanitizing solution from said container to said sanitizing rollers, said hose extending vertically between said container and said sanitizing rollers.

5. The system of claim 1, wherein said sanitizing rollers rotate simultaneously with said handrail.

6. The system of claim 1, wherein said housing includes lights, said lights emitting different predetermined customizable colors, said curvature curving away from said lights, said lights extending an entire height of said housing along lateral sides of said housing.

7. The system of claim 6, wherein said lights are steady.

8. The system of claim 6, wherein said lights flash in a predetermined pattern.

9. The system of claim 1, wherein said housing includes at least one speaker for emitting sounds, said at least one speaker located at a top end of said housing, said at least one speaker extending a partial width of said housing.

10. The system of claim 9, wherein said housing includes at least one camera, said at least one camera capable of capturing pictures or video, said at least one camera being entirely above of said housing, said at least one camera being entirely above of said at least one speaker.

11. The system of claim 10, wherein said housing includes a display, said display providing real time news, information, alerts and notifications to users, said display being atop of said housing and extending outwardly therefrom, said at least one speaker and said display being adjacent to each other, said camera being centrally located at a top portion of said display.

12. The system of claim 11, wherein said display, said at least one camera and said at least one speaker are entirely above of said sanitizing rollers and said curvature.

13. The system of claim 11, wherein said display is a screen.

14. The system of claim 11, wherein said display is an advertising board configured to display advertisements to said users.

15. The system of claim 6, wherein guards extend outwardly and away from laterals sides of said curvature, said guards partially covering said handrail, said sanitizing rollers being in between said guards, said guards being curved, said guards curving towards said housing.

16. The system of claim 2, wherein secured atop of said container is a compartment, said compartment being in constant abutting contact with said container, said compartment partially covering a top region of said container, said compartment extending a partial width and a partial length of said container, said compartment having a height less than said container.

17. The system of claim 2, wherein an external container is secured externally to said housing, said external container being adjacent to said housing, said external container being in fluid communication with said container using an external hose, said external container housing additional of said sanitizing solution within to be supplied to said container, said external hose being partially exposed between said housing and said external container.

18. The system of claim 17, wherein said external container includes a container viewing window allowing a view of the interior of said external container to determine when said external container needs to be refilled with additional of said sanitizing solution, said container viewing window extending a partial height of said external container and being located along a lateral side of said external container.

19. The system of claim 2, wherein a sanitizer dispenser is secured to a front face of said housing, said sanitizer dispenser being recessed within said housing, said sanitizer dispenser being in fluid communication with said container, said sanitizer dispenser selectively dispensing said sanitizing solution when actuated by users, said sanitizer dispenser includes a nozzle to dispense said sanitizing solution, said nozzle being partially visible and extending outwardly from said sanitizer dispenser.

20. A sanitizing system, consisting of:
a. a handrail;
b. a housing assembly including a housing, said housing including a curvature on a rear side that cooperates with a shape of said handrail, said housing being secured to said handrail, said housing further including lights at lateral sides thereof, said lights extending an entire height of said housing, said housing further including a display at a top end of said housing, said display protruding from said housing, said housing including at least one speaker the top end of said housing adjacent to said display, said at least one speaker extending a partial width of said housing, said display having at least one camera centrally secured to the top portion of said display, said at least one camera being entirely above of said at least one speaker, said display, said at least one speaker and said at least one camera being entirely above of said curvature, said housing further including guards extending outwardly and away from lateral sides of said curvature, said guards being curved towards said lights; and
c. a sanitizing assembly including sanitizing rollers secured entirely within the periphery of the rear side of said housing along said curvature, said sanitizing rollers being entirely on the same plane and centrally located along said curvature adjacent to each other, wherein a cut portion is formed onto the rear side of housing exposing each of the sanitizing rollers thereof, wherein a hose is operatively coupled to a lateral side of each of the sanitizing rollers thereof, said sanitizing assembly further including a container secured within said housing containing a sanitizing solution within, said container being entirely below said curvature and sanitizing rollers, the hose being attached in fluid communication with said container and said sanitizing rollers, said hose delivering the sanitizing solution to the sanitizing rollers thereby said sanitizing rollers being soaked in the sanitizing solution, said container including a compartment secured atop thereof, said compartment partially covering a top region of said container, an external container secured adjacently to said housing, said external container being in fluid communication with said container using an external hose, said external container housing additional of said sanitizing solution within to be supplied to said container, said external hose being partially exposed between said housing and said external container, said external container including a viewing window permitting viewing of the interior of the external container, said viewing window extending a partial height of said external container, a sanitizer dispenser secured to a front face of said housing, said sanitizer dispenser recessed within said housing, said sanitizer dispenser being in fluid communication with said container, said sanitizer dispenser selectively dispensing said sanitizing solution when actuated by users, said sanitizer dispenser includes a nozzle to dispense said sanitizing solution, said nozzle being partially visible and extending outwardly from said sanitizer dispenser, said sanitizing rollers being in abutting contact with said handrail to dispense said sanitizing solution onto an outer surface of said handrail as the handrail rotates for sanitation of said handrail, said sanitizing rollers rotating simultaneously with said handrail.

* * * * *